United States Patent [19]

Kirchner et al.

[11] Patent Number: 5,202,506
[45] Date of Patent: Apr. 13, 1993

[54] OXIDATIVE DROWN PROCESS FOR 2-PERFLUOROALKYLETHYL ALCOHOLS

[75] Inventors: Jack R. Kirchner; Leonard H. Beck, both of Wilmington; James E. Dowd, Newark, all of Del.

[73] Assignee: E. I. du Pont de Nemours and Company, Wilmington, Del.

[21] Appl. No.: 864,819

[22] Filed: Apr. 2, 1992

[51] Int. Cl.$^5$ .................. C07C 31/40; C07C 31/38
[52] U.S. Cl. ................... 568/842; 568/812; 568/841
[58] Field of Search .............. 568/812, 842, 841

[56] References Cited

U.S. PATENT DOCUMENTS

| | | | |
|---|---|---|---|
| 3,283,012 | 11/1963 | Day | 260/633 |
| 4,001,309 | 1/1977 | Hayashi et al. | 260/493 |
| 4,219,681 | 8/1980 | Schwenk et al. | 568/842 |
| 4,613,681 | 9/1986 | Foulletier et al. | 560/236 |
| 4,618,731 | 10/1986 | Beck | 568/842 |
| 5,097,090 | 3/1992 | Beck | 568/842 |

FOREIGN PATENT DOCUMENTS

| | | |
|---|---|---|
| 245133 | 4/1986 | European Pat. Off. |
| 2318677 | 11/1974 | Fed. Rep. of Germany |
| 3035641 | 9/1980 | Fed. Rep. of Germany |
| 5047912 | 4/1975 | Japan ................. 568/812 |
| 5509025 | 8/1983 | Japan |
| 1527156 | 10/1978 | United Kingdom |

OTHER PUBLICATIONS

Hachman et. "J. Amer. Chem. Soc.", vol. 69 (1947) pp. 2022–2025.

*Primary Examiner*—Werren B. Lone

[57] ABSTRACT

A process for the formation of perfluoroalkylethyl alcohols from perfluoroalkylethyl iodides is disclosed. The process involves treatment of the perfluoroalkylethyl iodide with oleum.

4 Claims, No Drawings

OXIDATIVE DROWN PROCESS FOR 2-PERFLUOROALKYLETHYL ALCOHOLS

BACKGROUND OF THE INVENTION

1. Field of the Invention

This invention relates to the field of preparing 2-perfluoroalkylethyl alcohols through sulfation and hydrolysis of 2-perfluoroalkylethyl iodides and more specifically where an oxidant is part of the quench in the hydrolysis step.

2. Description of the Related Art 2-perfluoroalkylethyl alcohols (FA) are intermediates in the production of stain and oil resistant finishes for carpets and other such goods. Current processes for the production of 2-perfluoroalkylethyl alcohols incorporate a sulfation step and a hydrolysis step. In the sulfation step, 2-perfluoroalkylethyl iodides (PFAI) are reacted with sulfur trioxide. The fluorinated reactant is typically a perfluoroalkylethyl iodide mixture of the formula $F(CF_2)_{2x}CH_2CH_2I$, wherein X is an integer from 1-10. The homologue distribution can vary, but a product mixture wherein X is predominantly 3, 4 and 5 is typically used. The sulfur trioxide is typically utilized as a 65% solution in concentrated sulfuric acid known as oleum, but not limited thereto. The sulfation reaction can be carried out with $SO_3$ per se or with more or less concentrated oleum mixtures provided reaction stoichiometry requirements are satisfied. Specific reactant type/amount should be dictated by economic/process/safety considerations. In the hydrolysis step, the sulfation mass is drowned in water containing sodium sulfite to give 2-perfluoroalkylethyl alcohols.

During these reactions, various undesirable side products are formed, including 2-perfluoroalkylethyl iodides, the starting material. The 2-perfluoroalkylethyl iodides are not unused starting material, but instead are regenerated when iodide reacts with an unavoidable intermediate, such as perfluoroalkylethylsulfate or perfluoroalkylethyl bis sulfate.

This process is described in U.S. Pat. No. 3,283,012 by Day. This patent describes two reactions which are carried out in sequence. The first is the reaction of the iodide $R_fCH_2CH_2I$ with the oleum to form the fluoroalkyl hydrogen sulfate ester $R_fCH_2CH_2OSO_2OH$ and $I_2$. The second reaction is the hydrolysis of the ester with aqueous acid to the alcohol, $R_fCH_2CH_2OH$, and sulfuric acid.

Beck, in U.S. Pat. No. 4,618,731, teaches an improved process for the purification of 2-perfluoroalkylethanols in which unreacted iodides, having the formula $R_fCH_2CH_2I$ and $R_fI$, are reacted with an excess of an alkali metal hydroxide and a $C_1$-$C_3$ alcohol in a closed vessel at a temperature above 80° C. until neither of said iodides can be detected in said 2-perfluoroalkylethanols.

The methods taught by Day and Beck contain somewhat undesirable options. Day's process does not use an oxidant in the hydrolysis step and, therefore, iodides are found in the product mixture. Because of this additional purification steps are be needed to obtain high purity product.

Beck's process is simply for purification of the alcohols. Use of this process, although it would give high purity alcohols, would result in longer processing times.

Beck, in U.S. application Ser. No. 07/530,351, filed May 30, 1990, discusses an improvement to Day's process using two similar continuous reactor systems combined in series, in each of which the reactants are contacted in zones of intense agitation in low-volume loops operated under pressure and at high rates of recycle. This method does not involve new chemicals and does not discuss the use of an oxidant in the hydrolysis step.

Foulletier et al., in U.S. Pat. No. 4,613,681, and Hoechst AG DE 3035641, describe the use of percarboxylic acids, both expensive and hazardous to use, for the conversion of the iodides to esters and alcohols. Also, this reaction is performed in an organic solvent.

Schwenk et al., in U.S. Pat. No. 4,219,681, describes the use of water in the presence of N-methyl-2-pyrrolidone for the conversion of 2-perfluoroalkylethyl iodides to alcohols. Yield of desired product is relatively low and distillation is required to recover the solvent and to separate the product alcohol from by product olefin.

Hayashi et al., in U.S. Pat. No. 4,001,309, report the use of water and various amides for the conversion of 2-perfluoroalkylethyl iodides to mixtures of 2-perfluoroalkylethyl alcohols and 2-perfluoroalkylethyl esters, the latter being converted to the alcohols by treatment with an alkali. The use of the relatively expensive organic amides and of high temperatures and pressures detract from this method.

In Allied Chemical Corp. DT 2628705, a process is described in which the iodides are treated with sulfur trioxide in sulfur dioxide. This method requires refrigeration and conversion is not complete.

Farbwerke Hoechst AG DT 2318677 discloses a hydrolysis at high temperatures and pressures resulting in a product or relatively low purity.

Atochem EP 245133A describes an electro chemical treatment of the iodide which also results in a relatively low purity alcohol.

Daikin Kogyo KK J55009025 discloses a process in which the iodide is sulfonated using chlorosulfonic acid. By-product gaseous hydrogen chloride must be collected and conversion of the iodide is relatively low.

Asahi Glass KK J50047912 reports the reaction of perfluoroalkyl iodides with water in the presence of acids and dimethyl formamide. Product purity is low.

SUMMARY OF THE INVENTION

This invention is an improvement to the process of making 2-perfluoroalkylethyl alcohols through the sulfation and hydrolysis of 2-perfluoroalkylethyl iodides wherein an oxidant is added to the hydrolysis step to decrease the amount of iodide impurities found in the final product. The presence of an oxidant also prevents the formation of sulfur impurities, via the reaction:

$$SO_2 + HI \rightarrow sulfur.$$

The oxidant in this case is typically hydrogen peroxide, iodic acid, monopersulfuric (Caro's) acid, or periodic acid. Hydrogen peroxide is commercially available as a 30-70% solution in water. Iodic and/or monopersulfuric acids can be/are generated in situ on addition of an oleum-containing sulfation mass to an aqueous hydrogen peroxide-containing quench solution. Iodic acid is also obtained on addition of an acid-containing sulfation mass to an aqueous solution of an iodate salt, i.e. sodium or potassium iodate. Periodic acid is a commercially available strong oxidant. All cited oxidants are advantageous in that they introduce no new elements to the process. The specific choice of oxidant is dictated by cost, availability, effectiveness, etc. considerations.

DETAILED DESCRIPTION OF THE INVENTION

Overview

This invention is an improvement to the process of making 2-perfluoroalkylethyl alcohols through the sulfation and hydrolysis of 2-perfluoroalkylethyl iodides wherein an oxidant is added to the hydrolysis step to decrease the amount of iodide impurities found in the final product. Steps of the Process The process for preparing 2-perfluoroalkylethyl alcohol includes using a sulfation reaction vessel equipped with a stirrer for agitation, with mechanisms for heating and cooling, and with a temperature reading device, adding oleum to the sulfation reaction vessel, adding 2-perfluoroalkylethyl iodide to the oleum in the sulfation reaction vessel, while maintaining the temperature in the vessel at from 40° to 70° C. and the pressure of from 1 atm to 6 atm.

Using a second hydrolysis reaction vessel also equipped with mechanisms for heating, cooling and agitation and with a temperature reading device, adding water and an oxidant to the hydrolysis reaction vessel, transferring the sulfation reaction mass to the water and oxidant in the hydrolysis reaction vessel while maintaining the temperature in the vessel at from 50° to 130° C. and the pressure at from 1 atm to 5 atm for 10 to 30 minutes.

The mole ratio of $SO_3$ to perfluoroalkylethyl iodide should be from 2:1 to 10:1 and the mole ratio of oxidant to the initial perfluoroalkylethyliodide should be from 0.125:1 to 1:1. The amount of water in the quench step should be enough to bring the $SO_3$ content below 30% calculated as sulfuric acid.

Description of the Process Steps

The reaction vessel used for the sulfation reaction can vary in size depending on the amount of reactants used. It should, however, be at least half as large as the hydrolysis reaction vessel.

65% oleum is used for the sulfation reaction. Oleum is a solution of sulfur trioxide in concentrated sulfuric acid and should be handled very carefully.

2-perfluoroalkylethyl iodide should be added to the oleum slowly to prevent foaming and excessive temperature increases.

The hydrolysis reaction vessel should be large enough to hold the volumes of the quench solution and the sulfation reaction mass.

Water and oxidant, the constituents of the quench solution, are added to the hydrolysis reaction vessel in large enough quantities to repress the formation of hydrogen iodide. The preferred oxidants for use in this application are hydrogen peroxide, iodate ion, Caro's acid, and periodic acid.

The sulfation reaction mass can be transferred to the hydrolysis reaction vessel by any means suitable.

EXAMPLES

Examples 1 through 3 were performed under pressure, while Examples 4 through 6 were performed at atmospheric pressure. Examples 2 and 4 used no oxidant in the hydrolysis step, while Example 1 used sodium iodate, which forms iodate ion, as the oxidant and Examples 3, 5 and 6 used hydrogen peroxide as the oxidant. Also, in Examples 4 and 5, the perfluoroalkylethyl iodide $(F(CF_2)_{2x}CH_2CH_2I)$ homologue where X is primarily 3, 4 and 5, was used, while in Example 6, the homologue where X is primarily 3 and 4 was used.

EXAMPLE 1

65% oleum was added to a 5 gallon (0.0189 m$^3$) glass vessel equipped with a thermocouple, a pressure gauge, a nitrogen/vacuum line, a transfer line, a heating and cooling jacket, and an agitator. The pressure in the vessel was decreased to 0 psig and the contents of the vessel were heated to 32° C. 2-perfluoroalkylethyl iodide was added to the vessel over approximately 45 minutes to make a reaction mixture of 3 parts oleum to 1 part 2-perfluoroalkylethyl iodide.

Into a second 10 gallon (0.0379 m$^3$) glass vessel, which was connected to the first vessel via the transfer line and was equipped with a thermocouple, a pressure gauge, steam heating, and a blow-thru valve, were added sodium iodate and water. The water was in an 8 to 1 ratio with 2-perfluoroalkylethyl iodide and the sodium iodate was in a 1 to 8 molar ratio with 2-perfluoroalkylethyl iodide. The contents of the second vessel were heated to 60° C.

All of the contents of the first vessel were transferred to the second vessel through the transfer line by increasing the N$_2$ pressure in the first vessel. The temperature of the mass increased, due to the reaction exotherm, to 105° C. From there the reaction mass was heated to 110° C., where it was held for 4 hours. After 4 hours, a 1 to 4 solution of sodium sulfite to water was pumped into the vessel. This mass was held at 110° C. for one hour.

The mass was cooled and 2-perfluoroalkylethyl alcohol was separated. The acid layer was also separated. The yields and purities for this run were as follows:

| Yield: | 97.7% (bulk) |
| --- | --- |
| | 91.8% (100%) |
| Purity: | 93.9% 2-perfluoroalkylethyl alcohol |
| | 0.9% 2-perfluoroalkylethyl iodide |
| | 1.0% ethers |

EXAMPLE 2

Using the same equipment as in Example 1, 65% oleum was added to a 5 gallon (0.0189 m$^3$) glass vessel. The pressure in the vessel was decreased to 0 psig and the contents of the vessel were at 22° C. 2-perfluoroalkylethyl iodide was added to the vessel over approximately 45 minutes to make a 3 to 1 oleum to 2-perfluoroalkylethyl iodide reaction mixture.

Into the second vessel were added water and sodium sulfite. The water was in an 8 to 1 ratio with 2-perfluoroalkylethyl iodide, while the sodium sulfite was in a 1 to 80 ratio with 2-perfluoroalkylethyl iodide. This solution was heated to 52° C.

All of the contents of the first vessel were transferred to the second vessel. The reaction exotherm proceeded to raise the temperature of the mass to 110° C. The mass was held at this temperature for 2 hours. The reaction mass was then cooled and the product separated.

| Yield: | 97.3% (bulk) |
| --- | --- |
| | 92.0% (100%) |
| Purity: | 94.6% 2-perfluoroalkylethyl alcohol |
| | 1.6% 2-perfluoroalkylethyl iodide |
| | 0.6% ethers |

EXAMPLE 3

Using the same equipment as in Example 1, 65% oleum was added to the 5 gallon (0.0189 m$^3$) vessel. The pressure in the vessel was brought to 0 psig and the contents were heated. 2-perfluoroalkylethyl iodide was fed into the vessel to give a 3 parts oleum to 1 part 2-perfluoroalkylethyl iodide reaction mixture.

H$_2$O$_2$ and water were added to the second vessel and kept at 13° C. Enough water was used to make an 8 to 1 water to 2-perfluoroalkylethyl iodide ratio and enough H$_2$O$_2$ was added to make a 1.25 to 8 H$_2$O$_2$ to 2-perfluoroalkylethyl iodide ratio. The contents of the first vessel were then transferred to the second vessel by increasing the N$_2$ pressure in the first vessel. The temperature of this mass increased to 110° C., due to the reaction exotherm, and was held there for 2 hours. After 2 hours, the mass was cooled.

An attempt was made to separate the 2-perfluoroalkylethyl alcohol from the aqueous layer. The layers, however, were too dark to see a separation due to the presence of iodine. Samples were taken. The yields on this run were not available due to the inability to obtain a good separation of the alcohol and aqueous layers. The purities were as follows:

| Purity: | 96.5% 2-perfluoroalkylethyl alcohol |
|---|---|
| | 0.14% 2-perfluoroalkylethyl iodide |
| | 0.7% ethers |

EXAMPLE 4

A reaction vessel vented to the atmosphere through a water cooled condenser system was sequentially charged with oleum (nominal 65%) and 2-perfluoroalkylethyl iodides (PFAI where X=3, 4, 5) to obtain a two part oleum to one part PFAI reaction mixture. The reaction vessel charge was agitated and maintained at about 50° C. during the 15 minutes PFAI mixture addition period and a subsequent 45 minute hold period. The resultant reaction mass was then added over a 25 minute period, at atmospheric pressure, to an agitated reaction vessel containing aqueous sodium sulfite solution in an amount equivalent to about 6 parts water and 0.14 parts sodium sulfite per part PFAI mixture. The resultant mixture was heated to and held at reflux for about 3 hours, then sequentially cooled to about 85° C. with agitation, and to about 25° C. without agitation, to obtain the crude 2-perfluoroalkylethyl alcohol (FA) product mixture as a solidified mass having the following area percent composition by GC analysis.

| Homologue | Area Percent | |
|---|---|---|
| | FA | PFAI |
| 4 | 0.81 | |
| 6 | 31.08 | 1.31 |
| 8 | 29.20 | 1.51 |
| 10 | 17.28 | 0.99 |
| 12 | 8.24 | 0.48 |
| 14 | 3.46 | 0.27 |
| 16 | 1.28 | 0.10 |
| 18 | 0.26 | |
| | 91.61 | 4.66 |

| FA ethers | Area Percent |
|---|---|
| 6–6 | 0.39 |
| 6–8 | 0.61 |
| 8–8 | 0.60 |
| | 1.60 | where 4,6,8, ... correspond to the number of perfluorinated carbon atoms in the perfluoroalkyl segment and FA ethers represent perfluoroalkylethyl ethers.

EXAMPLE 5

A reaction vessel vented to the atmosphere through a water cooled condenser system was sequentially charged with oleum (nominal 65%) and PFAI (x=3,4,5) to obtain a 2 part oleum to 1 part PFAI reaction mixture. The reaction vessel charge was agitated and maintained at about 47° C. during the 17 minute PFAI mixture addition and a subsequent 71 minute hold period. The resultant reaction mass was then added over a 31 minute period, at atmospheric pressure, to an agitated reaction vessel containing aqueous hydrogen peroxide in an amount equivalent to about 9 parts water and 0.11 parts 30% hydrogen peroxide solution per part PFAI mixture. The reaction mixture was heated to and held at reflux for about 3 hours to obtain a near colorless, two phase mixture in the reaction vessel and a wet iodine/organic condensate on the bottom fraction of the reaction vessel's water cooled condenser system. An aqueous sodium sulfite solution equivalent to 1 part water and 0.14 parts sodium sulfite per part PFAI mixture initially charged was added to the reaction vessel, and the resultant mixture heated at reflux until the condenser mass was solubilized and/or flushed back to the reaction vessel. The area percent composition (identified components) of the recovered organic product, as determined by GC analysis, follows:

| FA Homologue | Area Percent | |
|---|---|---|
| | FA | PFAI |
| 4 | 2.39 | nd |
| 6 | 32.97 | nd |
| 8 | 32.47 | nd |
| 10 | 18.70 | nd |
| 12 | 8.59 | nd |
| 14 | 3.11 | nd |
| 16 | 0.88 | nd |
| | 99.11 | |

| FA ethers | Area Percent |
|---|---|
| 6–6 | nd |
| 6–8 | 0.59 |
| 8–8 | nd |
| | 0.59 | where nd is not detected.

EXAMPLE 6

A reaction vessel vented to the atmosphere through a water cooled condenser system was sequentially charged with oleum (nominal 65%) and PFAI (X=3,4) to obtain a 2 part oleum to 1 part PFAI reaction mixture. The reaction vessel charge was agitated and maintained at about 44° C. during the 14 minute PFAI mixture addition and a subsequent 60 minute hold period. The resultant reaction mass was then added over a 28 minute period, at atmospheric pressure, to an agitated reaction vessel containing aqueous hydrogen peroxide in an amount equivalent to about 6 parts water and 0.21 parts 30% hydrogen peroxide solution per part PFAI mixture. The reaction mixture was heated to and held at reflux for an elapsed time of 70 minutes, then cooled and the organic fraction sampled for GC analysis. The reaction vessel condenser system was flushed with aqueous sodium sulfite solution to solubilize the iodine coating and to recover a small amount of organic product which was sampled for GC analysis. The area percent composition (identified components) of the recovered organic fractions are summarized below.

| | Organic Product Composition | | | |
|---|---|---|---|---|
| | Reaction Flask | | Condenser | |
| | FA | PFAI | FA | PFAI |
| Homologue | | | | |
| 4 | 2.59 | | 16.10 | |
| 6 | 47.89 | | 72.30 | 0.18 |
| 8 | 32.69 | | 9.33 | 0.06 |
| 10 | 10.34 | | 0.84 | |
| 12 | 2.45 | | 0.08 | |
| 14 | 0.51 | | | |
| | 96.46 | | 98.65 | 0.24 |
| FA ether | | | | |
| 6-6 | 0.20 | | | |
| 6-8 | 0.20 | | | |

| Organic Product Composition | | | |
|---|---|---|---|
| Reaction Flask | | Condenser | |
| FA | PFAI | FA | PFAI |
| 0.40 | | | |

We claim:

1. A process for converting 2-perfluoroalkylethyl iodide to 2-perfluoroalkylethyl alcohol comprising contacting 2-perfluoroalkylethyl iodide with oleum of a strength sufficient to provide a mole ratio of $SO_3$ to 2-perfluoroalkylethyl iodide of from about 2 to 1 to about 10 to 1 at about 50° C. to 130° C. to produce 2-perfluoroalkylethylsulfate, contacting the 2-perfluoroalkylethylsulfate with enough water to bring the $SO_3$ content to below 30% calculated as sulfuric acid and an oxidant of sufficient strength to produce 2-perfluoroalkylethylalcohol while minimizing the production of 2-perfluoroalkylethyl iodide.

2. The process of claim 1 wherein the oxidant is selected from the group consisting of hydrogen peroxide, iodic acid, monopersulfuric acid, and periodic acid.

3. The process of claim 2 wherein the perfluoroalkylethyl iodide has the formula $F(CF_2)_{2x}CH_2CH_2I$ where x is an integer from 1 to 10.

4. The process of claim 3 wherein x is predominantly 3-5.

* * * * *